US012693252B2

(12) United States Patent
Dilger

(10) Patent No.: US 12,693,252 B2
(45) Date of Patent: Jul. 28, 2026

(54) DEVICE AND METHOD FOR DETERMINING THE THERMAL CONDUCTIVITY OF A GAS, TANK ARRANGEMENT AND VEHICLE

(71) Applicant: AST (ADVANCED SENSOR TECHNOLOGIES) INTERNATIONAL ASSET GMBH, Calw-Hirsau (DE)

(72) Inventor: Stefan Dilger, Donaueschingen (DE)

(73) Assignee: AST (ADVANCED SENSOR TECHNOLOGIES) INTERNATIONAL ASSET GMBH., Calw-Hirsau (DE)

( * ) Notice: Subject to any disclaimer, the term of this patent is extended or adjusted under 35 U.S.C. 154(b) by 320 days.

(21) Appl. No.: 18/281,155

(22) PCT Filed: Mar. 7, 2022

(86) PCT No.: PCT/EP2022/055748
§ 371 (c)(1),
(2) Date: Sep. 8, 2023

(87) PCT Pub. No.: WO2022/189354
PCT Pub. Date: Sep. 15, 2022

(65) Prior Publication Data
US 2024/0151675 A1 May 9, 2024

(30) Foreign Application Priority Data
Mar. 9, 2021 (DE) ..................... 10 2021 105 681.0

(51) Int. Cl.
*G01N 27/18* (2006.01)
*G01M 3/00* (2006.01)
(Continued)

(52) U.S. Cl.
CPC ............ *G01N 27/18* (2013.01); *G01M 3/002* (2013.01); *G01N 33/005* (2013.01); *G01N 33/0062* (2013.01); *G01N 33/225* (2013.01)

(58) Field of Classification Search
CPC .... G01N 27/18; G01N 33/005; G01N 33/225; G01M 3/002; G01M 3/005; G01M 3/16
See application file for complete search history.

(56) References Cited

U.S. PATENT DOCUMENTS 5,379,630 A    1/1995  Lacey
12,411,100 B2 *  9/2025  Dilger .................... G01N 27/06
(Continued)

FOREIGN PATENT DOCUMENTS

DE        101 21 610 A1   11/2002
DE        101 23 920 A1   11/2002
(Continued)

OTHER PUBLICATIONS

Ates et al. "Three omega probe with auto-zeroing," 2016 IEEE 22nd International Symposium for Design and Technology in Electronic Packaging, IEEE. Oct. 20, 2016.*
(Continued)

*Primary Examiner* — Nathaniel J Kolb
(74) *Attorney, Agent, or Firm* — Oliff PLC

(57) ABSTRACT

A device for determining a hydrogen concentration or hydrogen mixture concentration includes: an electrical conductor arrangement which is designed such that it can be brought into contact with the fluid mixture at least in part and is realized in the form of a voltage divider having two elements, the first element being a first conductor which, at least in a current-carrying state, has a resistance value which is different from that of the second element, a measuring bridge comprising two voltage dividers connected in parallel, one of the voltage dividers being formed by the electrical
(Continued)

conductor arrangement, a control unit for applying an AC voltage to the measuring bridge, a voltage detection unit for detecting a bridge voltage, and an evaluation unit configured so as to determine the thermal conductivity of the hydrogen or hydrogen mixture by evaluating the bridge voltage using the 3-Omega method.

11 Claims, 8 Drawing Sheets

(51) Int. Cl.
| | | |
|---|---|---|
| *G01N 33/00* | (2006.01) | |
| *G01N 33/22* | (2006.01) | |

(56) References Cited

U.S. PATENT DOCUMENTS

| | | |
|---|---|---|
| 2003/0033861 A1 | 2/2003 | Eisenschmid et al. |
| 2023/0168215 A1 | 6/2023 | Dilger |

FOREIGN PATENT DOCUMENTS

| | | | | |
|---|---|---|---|---|
| DE | 10 2014 115 566 A1 | 5/2015 | | |
| DE | 10 2020 131 192 A1 | 11/2021 | | |
| EP | 0640830 A1 * | 3/1995 | .............. | G01W 1/14 |
| GB | 1 340 820 A | 12/1973 | | |
| JP | 2004-191164 A | 7/2004 | | |
| JP | 2008139092 A * | 6/2008 | | |

OTHER PUBLICATIONS

Yusibani et al. "Application of the Three-Omega Method to Measurement of Thermal Conductivity and Thermal Diffusivity of Hydrogen Gas," International Journal of Thermophysics; Journal of Thermophysics Properties and Thermophysics and Its Applications, Kluwer Academic Publishers, Mar. 5, 2009.*

Machine translation of JP 2008139092 (Year: 2008).*

Jun. 25, 2025 Office Action issued in European Patent Application No. 22 711 029.3.

Ates, I. et al., "Three omega Probe with Auto-zeroing," 2016 IEEE 22nd International Symposium for Design and Technology in Electronic Packaging (SIITME), Oct. 20-23, 2016 Oradea, Romania, pp. 63-65.

Yusibani, E. et al., "Application of the Three-Omega Method to Measurement of Thermal Conductivity and Thermal Diffusivity of Hydrogen Gas," Int. J. Thermophys., 2009, vol. 30, pp. 397-415.

Kommandur, S. et al., "A microbridge heater for low power gas sensing based on the 3-Omega technique," Sensors and Actuators A: Physical, vol. 233, 2015, pp. 231-238.

Jun. 27, 2022 International Search Report issued in International Patent Application No. PCT/EP2022/055748.

Jun. 27, 2022 Written Opinion of the International Searching Authority issued in International Patent Application No. PCT/EP2022/055748.

Dec. 20, 2022 Office Action issued in German Patent Application No. 10 2022 105 250.8.

Mar. 30, 2026 Office Action issued in Chinese Patent Application No. 202280020400.1.

* cited by examiner

Fig. 5

DEVICE AND METHOD FOR DETERMINING THE THERMAL CONDUCTIVITY OF A GAS, TANK ARRANGEMENT AND VEHICLE

The present invention relates to a device and a method for determining the thermal conductivity of a gas, in particular of a gas mixture formed from a plurality of gases, which in particular comprises hydrogen or is hydrogen, as well as to a tank arrangement and a vehicle.

Vehicles such as passenger cars or trucks are known which have a hydrogen drive. The fuel used in this case is hydrogen. In particular, a hydrogen combustion engine or a fuel cell can be provided as the energy source. The fuel cell in turn is usually followed by an electric motor to drive the vehicle. A hydrogen tank is provided for storing the hydrogen. This can be designed as a pressurized or liquid hydrogen accumulator tank, or the hydrogen is stored in metal hydrides. As a safety precaution, it is necessary to install leakage sensors on the vehicle which detect a possible leakage of hydrogen from the hydrogen tank.

In contrast, the invention is based on the object of creating a device with which a hydrogen concentration can be determined in a manner which is simple in terms of device technology. Furthermore, it is the object of the invention to create a tank arrangement for hydrogen and a vehicle comprising a hydrogen drive which both are simple in terms of device technology and can be used safely. Furthermore, a method for a technically simple and cost-effective measurement of a hydrogen concentration is to be created.

The object with regard to the device is achieved according to the features of claim 1, with regard to the tank arrangement according to the features of claim 5, with regard to the vehicle according to the features of claim 8 and with regard to the method according to the features of claim 9.

Further advantageous embodiments of the invention are subject matter of the dependent claims.

According to the invention, the thermal conductivity of hydrogen, in particular of a hydrogen mixture, such as hydrogen and air, is determined in order to draw a conclusion about the hydrogen concentration. For this purpose, a device for determining the thermal conductivity comprises an electrical conductor arrangement which is designed such that it can be brought into contact with the hydrogen or hydrogen mixture at least in part. The conductor arrangement is realized in the form of a voltage divider and has two elements. A voltage divider is preferably to be understood as a series circuit of passive electrical two-pole units by means of which an electrical voltage is divided.

The device according to the invention preferably has a measuring bridge with two voltage dividers connected in parallel, each having two elements. One of the voltage dividers is formed by the above-mentioned conductor arrangement. Furthermore, the device has a control unit for applying an AC voltage to the measuring bridge and a voltage detection unit for detecting a bridge voltage.

In addition, the device has an evaluation unit configured so as to determine the thermal conductivity and/or concentration of the hydrogen or hydrogen mixture by evaluating the bridge voltage using the 3-Omega method. By using the device, it can be determined whether the hydrogen or hydrogen mixture has a predetermined thermal conductivity or concentration, so that, for example, leakage from a hydrogen accumulator device can be determined. For this purpose, for example, a signal can be output, in particular via an appropriate means such as a display and/or a loudspeaker, if there is a hazard or if there is a predetermined concentration of the hydrogen or in case of a hydrogen concentration being greater than zero.

In its gaseous state, hydrogen has a comparatively high thermal conductivity compared to other gases, for example 0.186 W/mK. If hydrogen escapes from a hydrogen tank in the event of a leak, this leads to a change in the thermal conductivity of the atmosphere surrounding the hydrogen tank. In the event of a leak, the atmosphere contains air and hydrogen. Due to the comparatively high thermal conductivity of hydrogen, a change in the thermal conductivity of the atmosphere can be detected by the device with a high degree of measuring accuracy and thus a leak can be inferred. The device is designed to be simple and inexpensive, thus enabling a hydrogen detection which is simple and reliable in terms of device technology.

Preferably, the device is designed such that it can be arranged outside a tank space of the hydrogen tank in order to detect a leakage of hydrogen indirectly via the thermal conductivity.

The first element of the conductor arrangement is preferably a first conductor which has, at least in the current-carrying state, a resistance value which is different from that of the second element. Consequently, the measuring bridge is detuned when an AC voltage is applied to the measuring bridge, so that a bridge voltage can be detected by the voltage detection unit.

The second element of the conductor arrangement can be a second conductor, which in a currentless state has the same resistance value as the first conductor. In this regard, the two conductors are configured such that the first conductor heats up more than the second conductor in a current-carrying state.

According to another aspect, the second element may be a fixed resistor used in place of the second conductor. A fixed resistor is understood to be a resistor that does not substantially change its resistance value even in a current-carrying state, and thus can be considered to be substantially constant under any conditions. When a fixed resistor is used, the two resistors of the other voltage divider are designed such that their resistance value is adjustable or variable. Preferably, the two adjustable resistors are formed as digital potentiometers. In the current-carrying state, the first conductor heats up and therefore changes its resistance value, so that the first conductor and the fixed resistor have different resistance values in the current-carrying state. Here, the resistance value of the first conductor is preferably greater than that of the fixed resistor. However, the resistance value of the first conductor may also be smaller than that of the fixed resistor. When using a fixed resistor, the evaluation unit is configured such that it balances the two adjustable resistors before applying an AC voltage to the measuring bridge. This configuration has the advantage of reducing requirements with regard to manufacturing accuracy which is required, for instance, for the first and second conductors to have the same resistance value in a currentless state. In addition, a detection accuracy is increased because the measuring bridge is reliably balanced before the evaluation unit begins a to determine the thermal conductivity.

According to an aspect of the present invention, the hydrogen is part of a fluid mixture formed from at least two fluids, in particular at least two gases, in particular hydrogen and air, with the thermal conductivity preferably being known in each case. The evaluation unit may be configured to determine a concentration or a mixing ratio of the fluid mixture by comparing the thermal conductivity of the fluid mixture with the thermal conductivities of the two fluids from which the fluid mixture is mixed. Accordingly, a mixing ratio of the fluid mixture can be accurately determined. It should be noted that at least one of the two fluids may also be a fluid mixture, provided that the thermal conductivity thereof is known. The determination of a mixing ratio offers the advantage that the composition of the fluid mixture can be indicated to a user in an easily understandable manner.

According to another aspect of the present invention, the fluid is a fluid mixture preferably formed from two fluids, in particular air and hydrogen, each of which may have a known thermal conductivity. The evaluation unit may be configured such that it determines a freezing point of the fluid solution by comparing the thermal conductivity to a straight line. The straight line is obtained by linear interpolation using the thermal conductivity and the freezing point of the fluids as supporting points, respectively. To obtain the straight line, the values of the thermal conductivity of the two fluids are respectively plotted on an x-axis of a Cartesian coordinate system and the values of the freezing points of the two fluids are plotted on a y-axis of the Cartesian coordinate system. The determined value of the thermal conductivity of the fluid mixture formed from the two fluids is then also plotted on the x-axis, and the associated value of the freezing point of the thermal conductivity can consequently be determined as the y-axis value of the straight line at this point. This linear interpolation allows to determine the freezing point in an easy way and a user can accurately judge whether the fluid mixture is suitable for a particular temperature.

According to another aspect of the present invention, it is preferred that a cross-sectional area of the first conductor is smaller than that of the second conductor. This design of the two conductors easily ensures that the first conductor heats up more than the second conductor in a current-carrying condition.

According to an additional aspect of the present invention, the ratio between the cross-sectional areas of the first conductor and the second conductor may be in the range of 3 to 5, and preferably amounts to 4. However, the ratio of the cross-sectional areas of the first conductor and the second conductor may also be in the range of 2 to 6. This design of the first conductor and the second conductor ensures that the first conductor is sufficiently heated in order to allow good detection accuracy of the change in resistance.

According to an aspect of the present invention, it is preferred that the AC voltage is sinusoidal. Accordingly, the applied AC voltage can be generated in a simple manner and is suitable for processing in the 3-Omega method.

According to another aspect of the present invention, it is of advantage if a current intensity of a current flowing through the conductor arrangement is in the range of 150 mA to 250 mA and preferably amounts to 200 mA. However, the current intensity may also be in the range of 100 mA to 300 mA. By setting the current intensity to this range, a good adaptation of the device for an electrical system of a vehicle and a good detection accuracy of the resistance change is achieved.

According to a preferred aspect of the present invention, the first and second conductors may be arranged adjacent to each other. For example, they may mutually engage behind each other and/or so as to overlap each other. Preferably, the two conductors are arranged on a common support arrangement.

According to an aspect of the present invention, the first and second conductors are preferably arranged on a common circuit board or support arrangement.

On the circuit board or support arrangement, the first conductor and the second conductor may have a meandering configuration. A space-saving conductor arrangement is achieved by a meandering arrangement of one conductor or both conductors on the circuit board. In addition, the use of a standard circuit board (an FR4 circuit board, for instance) enables an inexpensive and easy-to-manufacture conductor arrangement.

If a conductor is formed to be meander-shaped, it has, for example, at least two legs at a parallel distance and/or adjacent to each other, which are connected via a connecting portion. Preferably, a plurality of such legs is provided, which are arranged adjacent to each other and are connected via connecting portions. Between the legs of the second conductor, for example, the first conductor may be arranged on the support arrangement. These two legs of the second conductor, between which the first conductor is arranged, can in this case be spaced apart from one another by a greater distance than the other legs. Preferably, the first conductor is then formed with two or more legs which are connected via one or more connecting portions. These legs can be arranged next to each other, preferably at a parallel distance. At least one or both conductors is/are advantageously arranged to be as compact as possible.

According to another aspect of the present invention, the first and/or the second conductor may be formed as wires. A wire is to be understood as a metallic conductor with a round or angular or flat or rectangular or profiled cross-section, which, if not arranged on a substrate or in a holder, is fully surrounded by the fluid mixture at least over a longitudinal portion of the wire. The conductors formed as a wire may be rigidly shaped, formed as a helix, or wound or bent in some other manner. It has been shown in experiments that the use of wires as first and/or second conductors significantly improves the detection accuracy, especially compared to the design in the form of conductive tracks. Even in case the wires are attached to a conductor track or to a substrate approximately like conductor tracks, the detection accuracy is improved. The helical shape also enables a compact design.

The conductors formed as wires or the conductor formed as a wire can be pre-stressed by means of at least one elastic element in order to compensate for a change in length that occurs due to heating in the current-carrying state or a change in length of the support arrangement due to a change in temperature. The elastic element can preferably be designed as a spring element. In this way, it can be prevented that the conductor(s) formed as wires come into contact with other conductive portions of the device or with themselves in case of a change in length or in case of a change in shape or length of the support arrangement. In this way, a short circuit of the wires can be reliably prevented.

According to a further advantageous aspect, the board or the support arrangement may be protected with a cover or a lid, which may be formed in such a way that the hydrogen or the hydrogen mixture whose thermal conductivity is to be determined can pass through to come into contact with the first and/or the second conductor. The cover or lid may be formed with slots or holes or openings for this purpose. Furthermore, the cover may prevent moving objects from hitting the conductor(s), thereby reliably preventing damage.

According to a further aspect of the present invention, the first conductor and the second conductor may be made of the same material. In this way, a simple manufacturing of the first conductor and the second conductor can be achieved and different material properties of the two conductors need not be considered.

According to an additional aspect of the present invention, the first conductor and the second conductor may be covered with an insulating layer. The insulating layer may be a lacquer or solder resist, which is a low-cost solution. In this way, an extremely compact arrangement of the conductors is achieved, since a short circuit between adjacent meanders or helical turns of the conductor arrangement is reliably prevented.

According to an additional aspect of the present invention, the control circuit is preferably formed inexpensively and simply from two transistor booster stages. In this way, the DC voltage used in a vehicle electrical on-board system can be converted to the AC voltage, preferably to a sinusoidal AC voltage.

According to a further aspect of the present invention, the evaluation unit may be configured so as to filter a signal portion of the bridge voltage having single and/or multiple frequency, preferably the triple frequency, of the AC voltage by means of a software-implemented synchronous rectifier. In this way, no hardware-implemented synchronous rectifier is required, which results in a cost saving for the device according to the invention.

The device is preferably designed as a module.

According to the invention, a tank arrangement is provided which comprises at least one device according to one or more of the preceding aspects. The tank arrangement has at least one fluid tank with at least one internal tank space which can be filled with a fluid. The fluid tank is configured, for example, as a pressure accumulator or as a liquid hydrogen accumulator or as an accumulator with metal hydrides or as an accumulator with nanotubes. It would also be conceivable to store the fluid, in particular in the form of hydrogen, via a chemical compound in the fluid tank. The device is preferably arranged outside the tank space so as to detect a possible outflow or leakage of the fluid, in particular in the form of a gas, by determining the thermal conductivity of the atmosphere surrounding the fluid tank.

In other words, a liquid container may comprise the device for determining the thermal conductivity of a fluid or fluid mixture. In this case, the device is not in operative communication with the interior of the container, i.e., the fluid/fluid mixture does not flow around it in the interior. On the contrary, the device is arranged in such a way that the conductor arrangement is in contact with the atmosphere surrounding the liquid container or in contact with the air or gas surrounding the fluid container. Accordingly, the change in thermal conductivity can be determined due to a fluid or fluid mixture escaping into the environment. In this way, it can be reliably determined whether hydrogen, for example, is leaking.

Preferably, the fluid tank is a hydrogen tank that can be filled with hydrogen. The hydrogen tank can be designed as a fuel cell, for example. The device is preferably set up to detect a leakage of hydrogen. This is advantageous because the device can detect hydrogen with a very high degree of certainty due to its comparatively high thermal conductivity. This occurs in particular due to a change in the thermal conductivity of the gas surrounding the hydrogen tank, which is contaminated with the hydrogen in the event of a leak.

In a further implementation of the invention, a plurality of the devices is provided which are spaced apart from each other. It occurs in different areas that the devices have their conductor arrangement in contact with the gas surrounding the fluid tank, in particular outside the fluid tank. Thus, safety is further increased since a larger area of the fluid tank can be monitored by the devices. It is conceivable that the devices could share one or more components, such as the evaluation unit. The conductor arrangement of the device is preferably not shared, whereby a respective conductor arrangement is provided for a respective device, each of which can be brought into contact with the fluid mixture.

According to the invention, a vehicle is provided with a hydrogen propulsion unit and the tank arrangement according to one or more of the aforementioned aspects. Owing to the tank arrangement, said vehicle can be used safely and be designed in a simple manner in terms of device technology.

The vehicle may be an aircraft or a water-borne vehicle or a land vehicle. The land vehicle may be a motor vehicle or a rail vehicle or a bicycle. Particularly preferably, the vehicle is a truck or a passenger vehicle or a motorcycle. The vehicle may further be configured as a non-autonomous or semi-autonomous or autonomous vehicle.

Preferably, a device is arranged adjacent to the hydrogen tank or fuel cell and/or a device in the area of the underbody of the vehicle—in particular on an inner side of the underbody—and/or a device in the area of the exhaust tract, in particular of the vehicle interior exhaust track. It has been shown that hydrogen accumulates at these positions in the event of a leak and is therefore easily detectable. If such a device is provided at all positions, reliable monitoring of the hydrogen tank can be made possible.

A method according to the invention for determining a thermal conductivity of hydrogen in a gas mixture with the device according to one or more of the preceding aspects or with a tank arrangement according to one or more of the preceding aspects comprises the following steps: Applying an AC voltage to a measuring bridge; detecting a bridge voltage; and determining a thermal conductivity of the gas mixture by evaluating the bridge voltage using the 3-Omega method.

In the event that the second element of the one voltage divider of the measuring bridge is designed as a fixed resistor and the two resistors of the other voltage divider of the measuring bridge are designed as adjustable resistors, according to one aspect of the invention, an initial step of balancing the measuring bridge may be performed. The evaluation unit may then be configured to cause at least one of the two transistor booster stages to apply a DC voltage to the measuring bridge. The DC voltage has a value of 200 mV. However, the value of the DC voltage may also be between 100 mV and 500 mV, inclusive. The bridge voltage is then detected and the evaluation unit changes the resistances of the two adjustable resistors. A DC voltage is then again applied to the measuring bridge and the bridge voltage is detected. This process is repeated until the bridge voltage detected in response to the applied DC voltage is substantially equal to a voltage of 0V. Consequently, the measuring bridge can be reliably balanced. Advantageously, this procedure is preferably performed during a first start-up or at a start of a detection of the thermal conductivity in order to initially calibrate the measuring bridge.

Alternatively or additionally, the evaluation unit may be designed so as to filter out a signal component of the bridge voltage which corresponds to the simple frequency of the AC voltage applied to the measuring bridge. The amplitude of this signal component of the bridge voltage can be used as a measure of the detuning of the measuring bridge, and the evaluation unit can be designed so as to change the resistance value of the adjustable resistors in such a manner that the signal component of the bridge voltage corresponding to the simple frequency of the applied AC voltage is substantially 0 V. This approach offers the advantage that detuning of the measuring bridge can be detected during a measuring operation. Consequently, detuning situations of the measuring bridge that occur, for example, as a result of heating during operation can be detected, and the measuring bridge can subsequently be calibrated.

Hereinafter, the present invention will be described in more detail with reference to the accompanying Figures in which:

FIG. 1 schematically shows a circuit diagram of a device for determining a thermal conductivity of a fluid mixture;

FIG. 4 and FIG. 5 show a measuring bridge with a conductor arrangement in which the first and second conductors are formed as wires;

Figure 1:
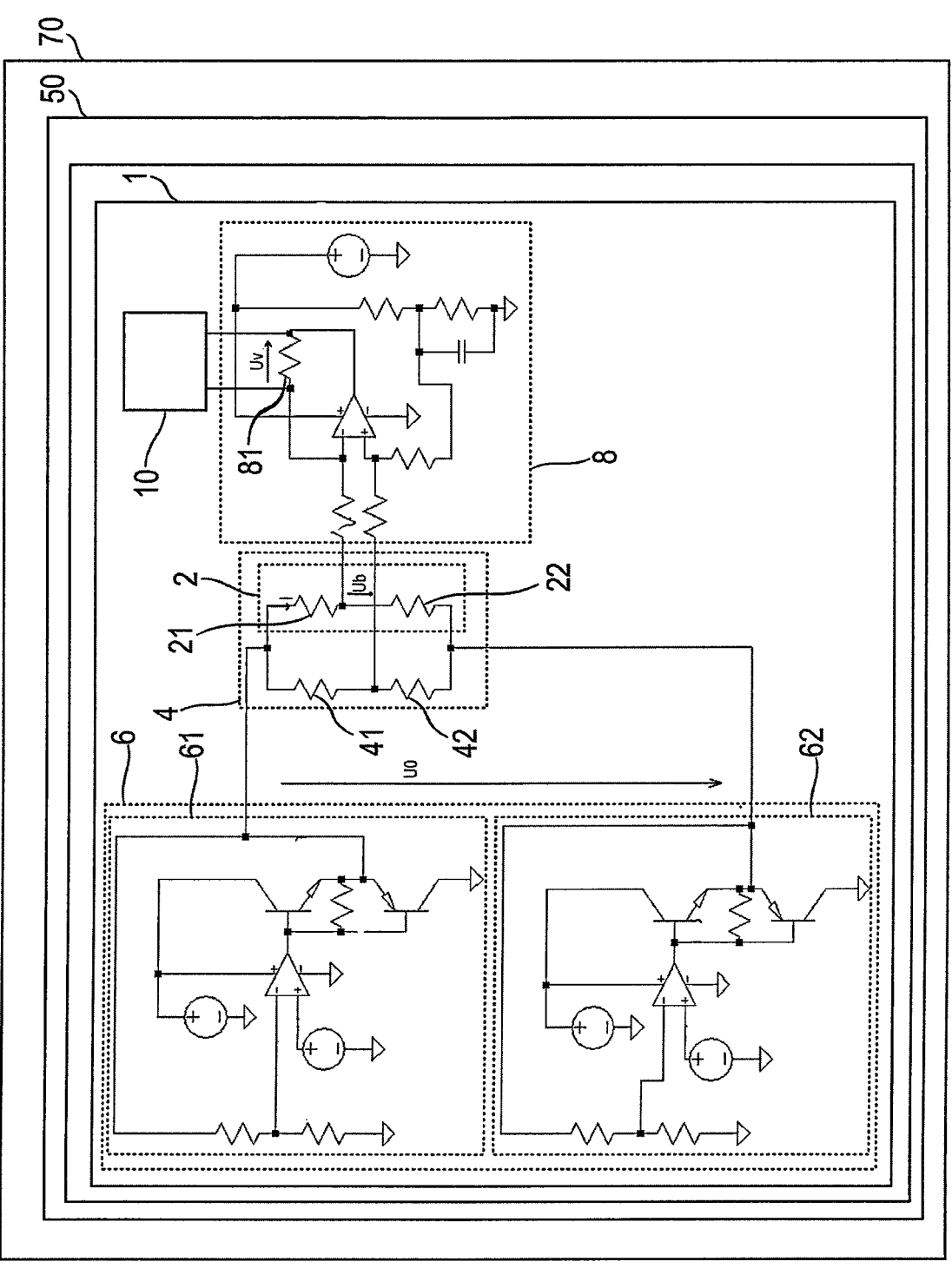

An embodiment of the present invention will be described below. FIG. 1 schematically shows a circuit diagram of a device 1 for determining a thermal conductivity of a fluid. In the present embodiment, the fluid is in particular a fluid mixture that can be formed from hydrogen and air. The fluid mixture may be formed when hydrogen unintentionally escapes from a fluid tank in the form of a hydrogen tank 50 of a vehicle 70 due to a leakage. Further, in accordance with the present embodiment, the device 1 is configured for use in a vehicle.

In the present embodiment, the thermal conductivity of the fluid mixture is used as a measure for the mixing ratio of hydrogen to air. Accordingly, a fluid mixture mixed from hydrogen and air has a thermal conductivity that is between the thermal conductivity of hydrogen and air, so that a conclusion about the mixing ratio of the fluid mixture can be drawn by comparing the determined thermal conductivity with a predetermined thermal conductivity.

For this purpose, the device 1 for determining a thermal conductivity of a fluid mixture formed from a plurality of fluids has an electrical conductor arrangement 2, a measuring bridge 4, a control unit 6, a voltage detection unit 8, and an evaluation unit 10.

Figure 2:
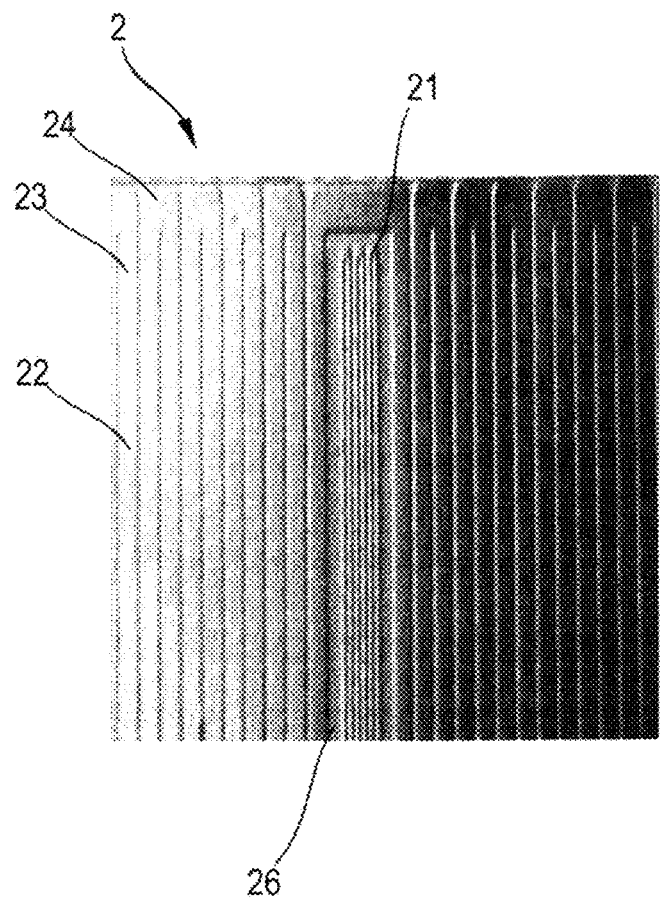
FIG. 2 shows a conductor arrangement according to one embodiment of the present invention with a first conductor and a second conductor that are mounted on a circuit board.

The electrical conductor arrangement 2 is designed such that it is at least partially in contact with the air or with the fluid mixture if hydrogen escapes. The electrical conductor arrangement 2 shown in FIGS. 1 and 2 is brought into contact with the air or the fluid mixture by being in contact with the air surrounding the hydrogen tank 50. The conductor arrangement 2 is thus not in contact with the tank's interior of the hydrogen tank 50, but with its surroundings. For this purpose, the device 1 is arranged or attached, for example, adjacent to the hydrogen tank 50 or on the outside thereof. It would also be conceivable to provide several devices 1 for monitoring the hydrogen tank 50.

The device 1 is preferably arranged on or near the hydrogen tank 50 in such a way that it can detect escaping hydrogen.

The electrical conductor arrangement 2 has a first conductor 21 and a second conductor 22 in a series connection. The first conductor 21 and the second conductor 22 have the same resistance value in a currentless state. Further, the two conductors 21, 22 are configured such that the first conductor 21 heats up more than the second conductor 22 in a current-carrying state.

In the present embodiment, the conductor arrangement 2 shown in FIG. 2 is used in which the two conductors 21, 22 are arranged in the form of conductor paths on a circuit board 26 in a meandering manner. To achieve a meandering arrangement, the two conductors 21 and 22 have a plurality of legs 23 and connecting portions 24 between these legs 23, as shown in FIG. 2. In the example of FIG. 2, the first conductor 21 is also arranged in a meandering manner between two, in particular middle, legs 23 of the second conductor 22. However, the arrangement of the two conductors 21 and 22 is not limited to the arrangement shown, and the two conductors 21 and 22 may, for example, be arranged in a meandering manner only in portions. Moreover, it is possible that only one of the two conductors 21, 22, preferably the second conductor 22, is arranged in a meandering manner. By applying the two conductors 21, 22 in the form of conductor tracks on the circuit board 26, for example on an FR4 circuit board by a known printing process, a low-cost and robust conductor arrangement 2 can be obtained. In addition, the meandering arrangement of the two conductors 21, 22 offers the advantage of a space-saving arrangement of the conductor arrangement 2 in the liquid container 30.

As can be seen in FIG. 2, a cross-sectional area of the first conductor 21 is smaller than that of the second conductor 22. Consequently, the second conductor 22 must be longer than the first conductor 21 by the factor by which the cross-sectional area of the second conductor 22 is larger than that of the first conductor 21, so that the first conductor 21 and the second conductor 22 have the same resistance value in the currentless state. In the electrical conductor arrangement 2 shown in FIG. 2, the cross-section of the second conductor 22 is larger by a factor of 4, so that the first conductor 21 must have 4 times the length to have the same resistance value. However, the factor is not limited to a factor of 4 and may, for example, be in the range of 3 to 5. Such a design of the two cross-sectional areas ensures sufficient detection accuracy in the case of a change in resistance in the current-carrying state described below.

In the present embodiment, the two conductors 21, 22 are implemented by conductor tracks made of copper. However, another material such as nickel, for example, may also be used. Preferably, the two conductors 21, 22 are made of the same material, so that any influence of different materials does not have to be considered in the dimensioning and the change in resistance in the current-carrying state described later. Moreover, if the same material is used, the fabrication of the electrical conductor arrangement 2 is simplified.

Furthermore, the first and second conductors 21, 22 are preferably covered with solder resist, so that a short circuit between the individual meanders of the first and second conductors 21, 22 due to the fluid mixture present therebetween is avoided.

When a current flows through the two conductors 21, 22 connected in series, the first conductor 21 is heated more than the second conductor 22 due to its smaller cross-sectional area. Consequently, a resistance value of the first conductor 21 increases more than the resistance value 22 of the second conductor. Since the conductor arrangement 2 is fully immersed in the fluid mixture, the amount of heating of the first conductor 21 also depends on a thermal conductivity of the fluid mixture. When the fluid mixture has a high thermal conductivity, the first conductor 21 heats up less than when the fluid mixture has a low thermal conductivity. Thus, a fluid mixture having a high thermal conductivity cools the first conductor 21 better than a fluid mixture having a low thermal conductivity. Accordingly, the magnitude of the change in resistance of the first conductor 21 can be used as a measure of the thermal conductivity of the fluid mixture.

In order to detect this change in resistance of the first conductor 21, as shown in FIG. 1, a measuring bridge 4 is used, which is designed, for example, as a Wheatstone-measuring bridge and has two voltage dividers connected in parallel, one of the voltage dividers being formed by the electrical conductor arrangement 2, i.e. by the series connection of the first conductor 21 and the second conductor 22. The other voltage divider is formed by two resistors R1 and R2 or 41 and 42, each having the same resistance value. The use of the measuring bridge 4 offers the advantage that a change in the resistance values of the first conductor 21 and the second conductor 22 due to a change in the ambient temperature is fully compensated.

To generate a current flow in the two conductors 21, 22, an AC voltage is applied to the measuring bridge 4 by the control unit 6. In the present embodiment, the control unit 6 is formed by two transistor booster stages 61, 62, so that it is possible to convert the DC voltage of the on-board electrical system of the vehicle 70 into an AC voltage. For this purpose, the first transistor booster stage 61 applies a positive voltage and the second transistor booster stage 62 applies a negative voltage alternately to the measuring bridge 4. In particular, the alternating voltage is a sinusoidal alternating voltage, so that the 3-Omega method described below can be carried out. The control unit 6 applies the AC voltage to the measuring bridge 4, so that a current in the range of approximately 200 mA flows in the series connection made up of the first and second conductors 21 and 22. However, the current intensity is not limited to this value and can be in the range of 150 mA to 250 mA, for example. The first conductor 21 heats up by a few Kelvin in the current-carrying state, which increases its resistance value, which in turn leads to detuning of the measuring bridge 4. Consequently, a bridge voltage Ub is present between the two voltage dividers, which is detected by the voltage detection unit 8. Preferably, the bridge voltage Ub is tapped between the resistors 41 and 42, on the one hand, and between the conductors 21 and 22 on the other.

In the present embodiment, as shown in FIG. 1, the voltage detection unit 8 is designed as an amplifier unit, in particular as a differential amplifier, in order to amplify the detected bridge voltage Ub by a predetermined factor, so that an amplified voltage Uv is obtained which is tapped at the resistor 81 by the evaluation unit 10. The amplified voltage Uv thus corresponds to the bridge voltage Ub—or the bridge voltage Ub can be inferred via the amplified voltage Uv—and a processing of the amplified voltage Uv is to be understood as a processing of the bridge voltage Ub.

In the present embodiment, the evaluation unit 10 is formed by a known microcontroller having RAM, ROM, CPU, I/O ports, A/D converter, etc. The evaluation unit 10 is configured to determine the thermal conductivity of the fluid mixture by evaluating the bridge voltage Ub or the amplified voltage Uv, which corresponds to the bridge voltage Ub, or via which the bridge voltage can be inferred, using the 3-Omega method.

The 3-Omega method was first described by Jason Randall Foley in 1999 in "The 3-Omega method as a nondestructive testing technique for composite material characterization". The contents thereof are incorporated herein by reference.

In the 3-Omega method, a metal wire in contact with a specimen, i.e., the first conductor 21, is used as both a heater and a thermometer. The AC voltage U0 is applied to the measuring bridge 4 by the control unit 6, as described above, so that a current I flows through first conductor 21 at the same frequency. Consequently, a power oscillating at twice the frequency is converted into heat in the first conductor 21, so that a temperature of the first conductor 21, and consequently also its resistance value, changes at twice the frequency of the applied AC voltage U0.

As a result, the measuring bridge 4 is detuned and the bridge voltage Ub, which also oscillates at twice the frequency like the resistance change, is generated. In the present embodiment, the resistance values of the two resistors 41, 42 forming the second voltage divider of the bridge circuit 4 as well as the resistance values of the first conductor 21 and the second conductor 22 are designed to have the same resistance value R in a currentless state. In addition, the second conductor 22 is designed such that its resistance value does not substantially change in the current-carrying state. This has the advantage that the bridge voltage is proportional to the change in resistance $\Delta R_{21}$ of the first conductor 21 and can be expressed by the following equation:

$$Ub = \frac{1}{4} \cdot \frac{\Delta R_{21}}{R} \cdot U0$$

Consequently, the bridge voltage Ub has a signal component that has three times the frequency of the AC voltage applied to measuring bridge 4. The filtering of this so-called 3-Omega signal component is done in software. The evaluation unit 10 is therefore configured such that it filters a signal component of the bridge voltage Ub which has a multiple frequency, preferably the triple frequency, of the AC voltage by means of a software-implemented synchronous rectifier.

According to the 3-Omega method, the amplitude of the signal with the triple frequency of the bridge voltage is a direct measure of the thermal conductivity of the fluid or fluid mixture. As mentioned above, the determined thermal conductivity for the fluid mixture lies between the two values for the thermal conductivity of hydrogen and air, so that it can be used as a measure of the mixing ratio. The determined thermal conductivity can then be compared to a predetermined thermal conductivity in order to assess whether hydrogen is present outside the hydrogen tank 50. If hydrogen is detected in the fluid mixture, a signal or alarm signal may be output.

The fluid mixture may be formed from the two fluids hydrogen and air, as described above, each of which has a known thermal conductivity. The evaluation unit 10 according to another embodiment may then also be configured to determine a concentration of the fluid mixture by comparing the thermal conductivity of the fluid mixture with the thermal conductivities of the two fluids.

Figure 3:
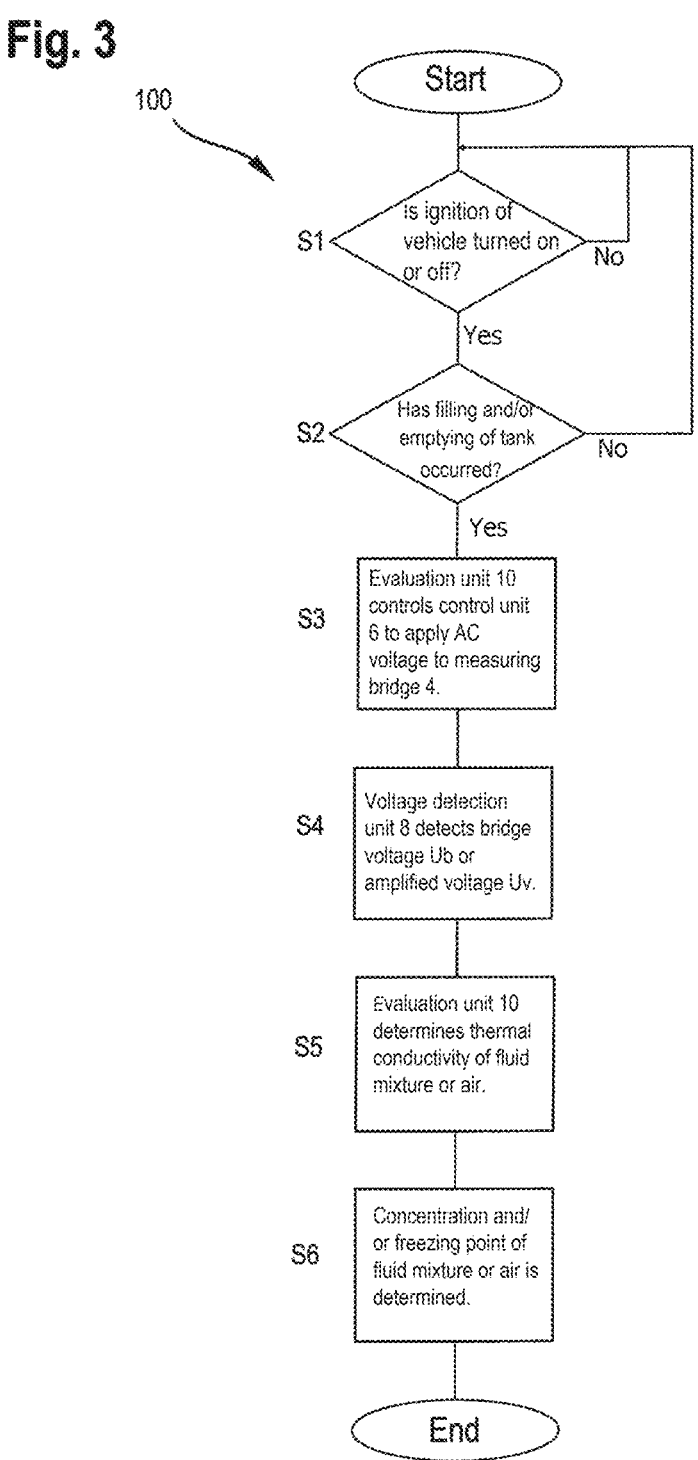
FIG. 3 shows a flowchart of a method for determining a thermal conductivity of a fluid using the first conductor and the second conductor.

Hereinafter, steps S1 to S6 of a method 100 for determining the thermal conductivity of a fluid or fluid mixture are described with reference to FIG. 3. In this regard, the evaluation unit 10 is configured to control the other components of the device 1 for determining the thermal conductivity, so that the individual steps S1 to S6 of the method 100 are executed. For the purpose of obtaining further information, the evaluation unit 10 is additionally capable of communicating with other units and means not shown, such as the detection means, which are installed in the vehicle 70 and are communicatively connected to each other via, for example, a vehicle bus. In this regard, the method 100 is stored in the form of software in the RAM or ROM and is executed by executing instructions by the CPU and outputting and receiving signals at the I/O ports.

In step S1, it is verified whether an ignition of the vehicle 70 is turned on and/or off. If it is not detected that the ignition is turned on and/or off (No in S1), the process waits until an appropriate signal is received. If the ignition is turned on and/or off (Yes in S1), S2 is executed.

In S2, based on a signal received from the detecting means, it is determined whether filling and/or emptying the hydrogen tank 50 is performed. If it is not determined that filling and/or emptying has occurred (No in S2), the processing returns to the beginning of the method. If it is determined that filling and/or emptying has occurred, processing goes to step S3.

It should be noted that the method 100 can also be executed without steps S1 and S2, so that the method 100 starts directly with step S3. In this case, the method 100 is repeated at a predetermined interval. The method 100 may also include only one of the two steps S1 or S2. The order of the two steps S1 and S2 can also be changed.

In S3, the evaluation unit 10 controls the control unit 6 to apply the AC voltage to the measuring bridge 4, and the method 100 proceeds to step S4.

In S4, the voltage detection unit 8 detects the bridge voltage Ub or an amplified voltage Uv corresponding to the bridge voltage Ub, and the method 100 goes to S5.

In S5, the evaluation unit 10 filters the signal portion of the voltage Uv corresponding to the triple frequency of the current applied to the measuring bridge 4 and determines therefrom the thermal conductivity of the fluid mixture or air if no hydrogen has leaked.

In S6, which can optionally be executed, the concentration and/or the freezing point of the fluid mixture is determined. However, it is not necessary that these parameters are determined, so that the method 100 can also be executed without step S6.

The device 1, the method 100 for determining a thermal conductivity of a fluid or the fluid mixture, and the hydrogen tank 50 have been described for use for the vehicle 70. It should be noted that the device 1 and the method 100 are not limited thereto and are applicable in any field in which a thermal conductivity of a fluid or fluid mixture is to be determined. Furthermore, the hydrogen tank 50 is not limited to an application in the vehicle 70.

Figure 4:
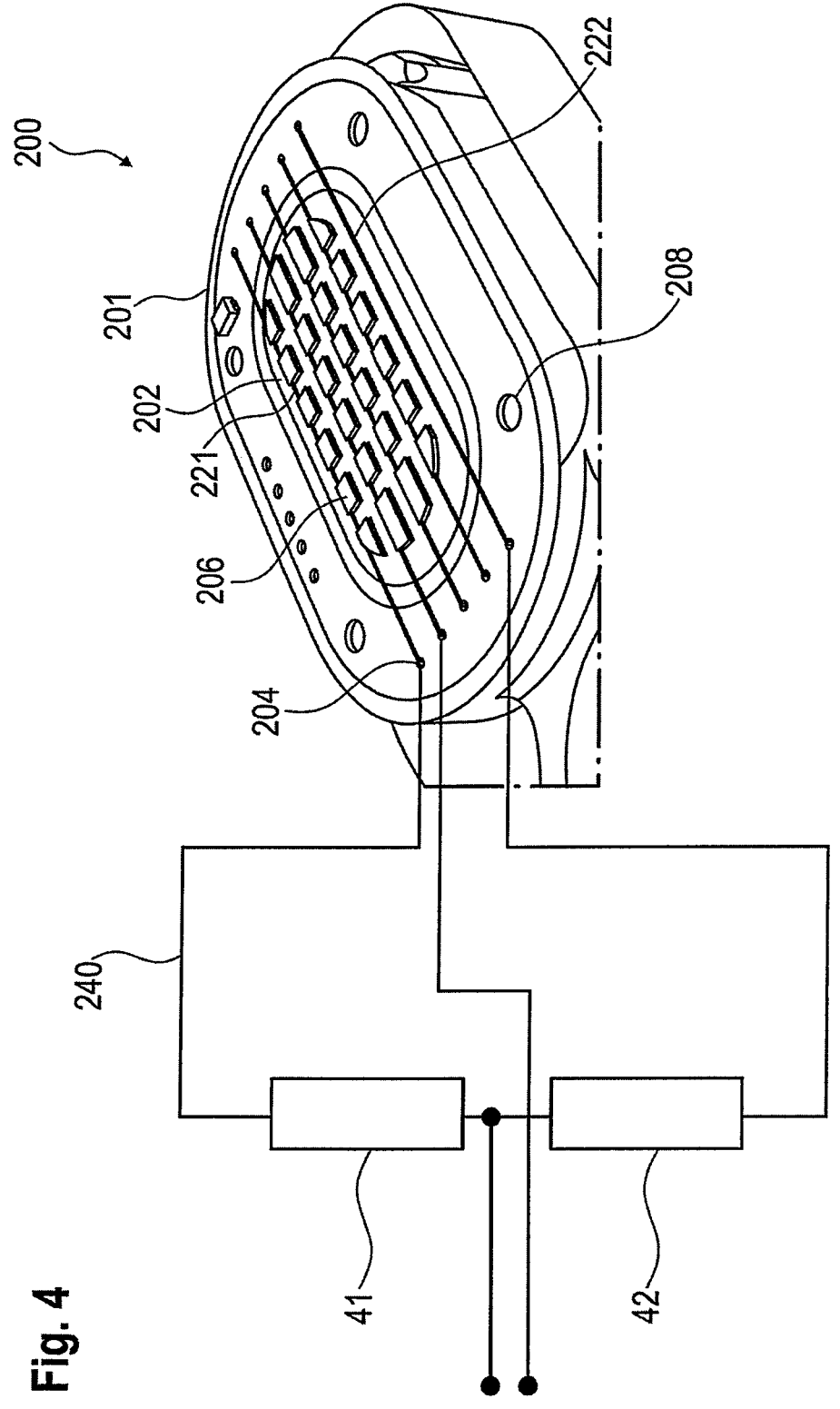
Figure 5:
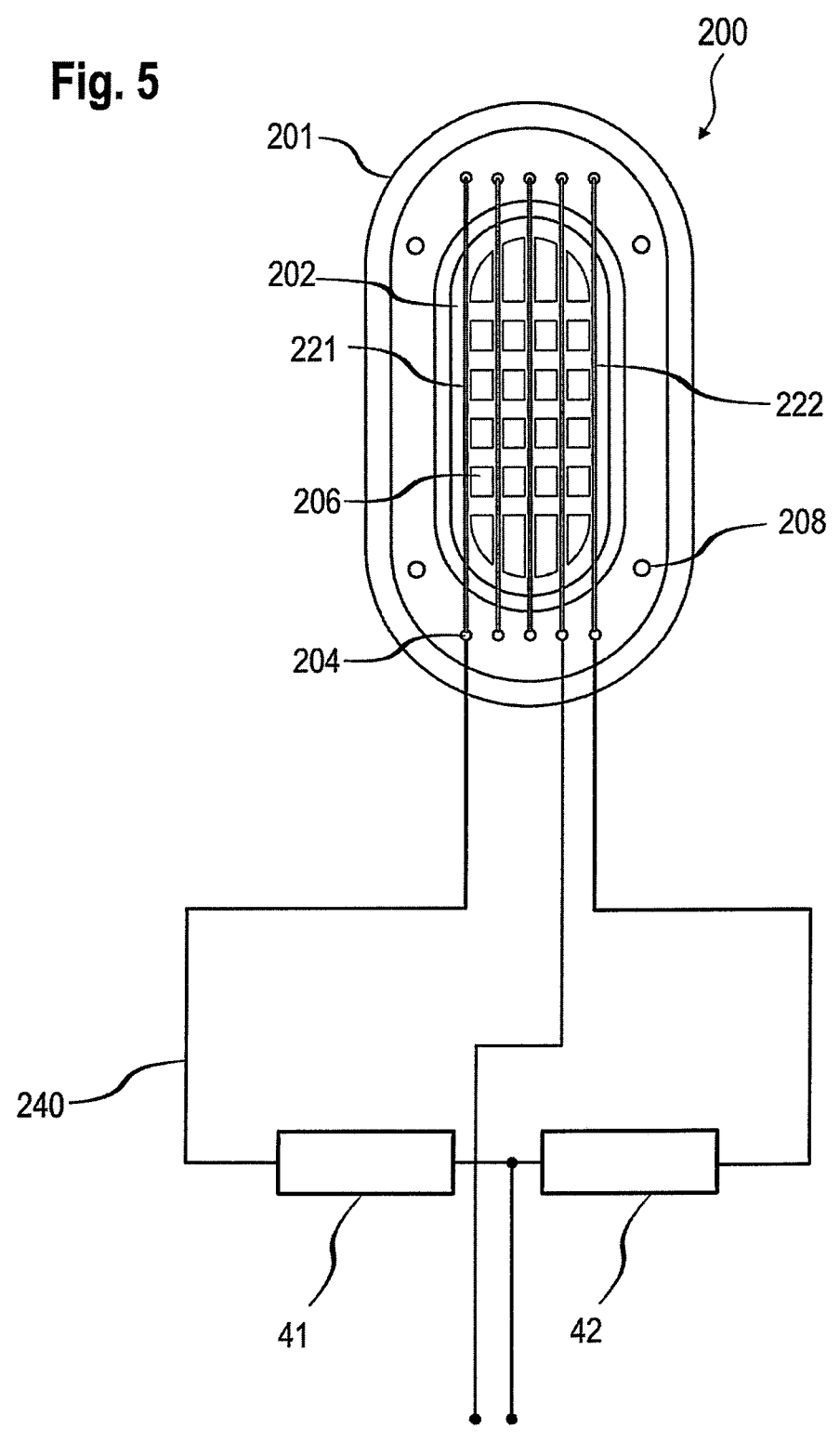

FIG. 4 and FIG. 5 show a measuring bridge 240 with a conductor arrangement 200, in which a first conductor 221 and a second conductor 222 are formed as wires. A wire is understood to be a metallic conductor with a round or angular cross-section that is attached to a support arrangement only at its two ends. The portion in between is fully surrounded by the fluid mixture.

In this case, the first conductor 221 has a length which is several times, preferably four times, the length of the second conductor 222 and for this reason has a cross-section which is smaller than the cross-section of the second conductor 222 by the ratio of the length of the first conductor 221 to the length of the second conductor 222. Accordingly, the first conductor 221 and the second conductor 222 have the same resistance value in a currentless state. In order to reduce the spatial extent of the conductor arrangement 200, the first conductor 221 is disposed on the conductor arrangement 200 in a meandering manner. It should be noted that the cross-section of the two conductors 221 and 222 in FIG. 4 and FIG. 5 is drawn the same for drawing reasons. The cross-sections of the two conductors 221 and 222 actually differ from each other.

The two conductors 221 and 222 are stretched over a recessed surface 202 of a support arrangement 201 in a plane parallel to the recessed surface 202, so that the fluid or fluid mixture fully surrounds and flows around them. In this way, the two conductors 221 and 222 are fully contactable with the fluid or fluid mixture. In this way, a detection accuracy of the thermal conductivity can be further improved by the device according to the invention.

In an edge region of the conductor arrangement 200, the two conductors 221 and 222 are led out via openings 204, preferably out of a sealed or opened interior, to form the individual meanders. The meander portions of the conductors 221, 222 led out of the openings 204 may extend parallel to each other and/or in a common plane. One or more elastic elements, e.g. spring elements (not shown), may be arranged in the conductor arrangement 200—for example in the interior—to mechanically bias the two conductors 221 and 222, so that a change in length due to heating in the current-carrying state is compensated, whereby both a change in length of the conductor arrangement 200 and a change in length of the two conductors 221 and 222 will be compensated. In this way, the two conductors 221 and 222 or adjacent meanders of the first conductor 221 can be prevented from contacting each other, and a short circuit can be reliably prevented in this way. In addition, a change in length or shape of the support arrangement 201 due to a change in temperature can also be compensated. The meandering portions of the conductors 221 and 222 led out of the openings 204 may have the same length.

One or more projections 206—preferably cuboidal ones—are arranged between the two conductors 221 and 222 and the meanders of the first conductor 221. The projections 206 extend from the recessed surface 202 to a plane that is also parallel to the recessed plane and further away from the recessed surface 202 than the plane in which the first and second conductors 221 and 222 are disposed. Accordingly, the protrusions 206 also prevent the first and second conductors 221 and 222 and the meanders of the first conductor 221 from coming into contact.

In other words, the projection(s) 206 is/are provided to reach beyond the conductors 221 and 222 projecting from the openings 204 to protect them. It would be conceivable to alternatively or additionally provide a cover with at least one fluid opening to protect the conductors 221 and 222. The advantage of the projection(s) is that, despite protection, the conductors 221 and 222 are practically exposed and can easily be brought into contact with a fluid/fluid mixture.

The two resistors 41 and 42 of the other branch of the measuring bridge 240 are designed as resistors with fixed resistance values. The resistance values of the two resistors 41 and 42 are selected such that the measuring bridge 240 is balanced in a currentless state. The two resistors 41 and 42 as well as the conductor arrangement 200 with the first and second conductors 221 and 222 can be arranged on a common arrangement, such as a common circuit board, or can be arranged so as to be spatially separated from each other and connected to each other via cables.

Holes 208 are formed in the edge region of the support arrangement 201, into which pins of a cover or lid (not shown) for the conductor arrangement 200 can be inserted. Alternatively, screws may also be threaded into the holes, in which threads are preferably formed, to connect the cover to the support arrangement 201. To further allow the fluid mixture to be brought into contact with the first and second conductors 221 and 222, the lid includes slots or holes through which the fluid mixture can flow to the first and second conductors 221 and 222. In addition, the lid can further reduce a risk of mechanical damage to the first and second conductors 221 and 222.

Figure 6:
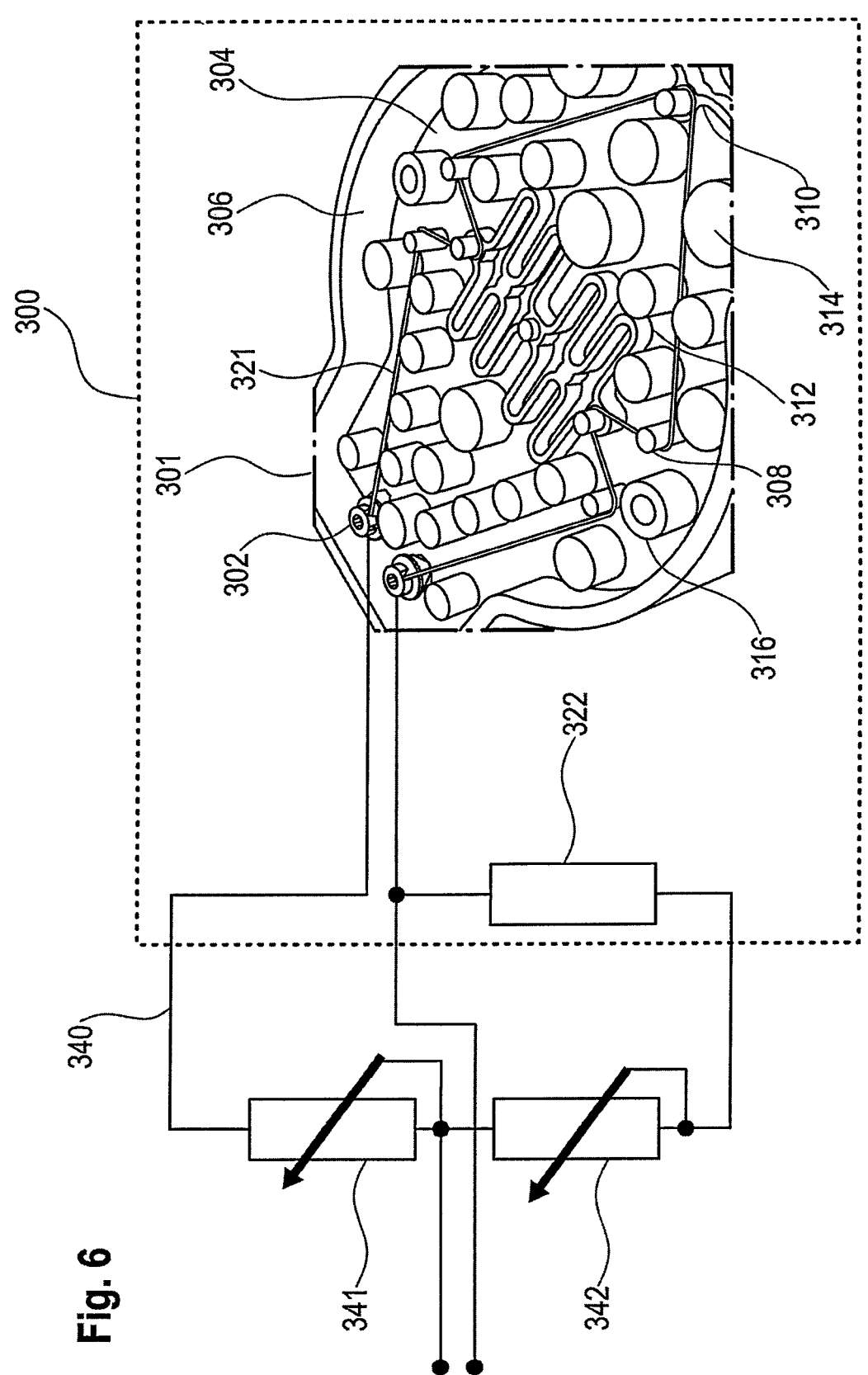
FIG. 6 and FIG. 7 show a measuring bridge with a conductor arrangement in which a first conductor formed as a wire and a fixed resistor are connected in series.
Figure 7:
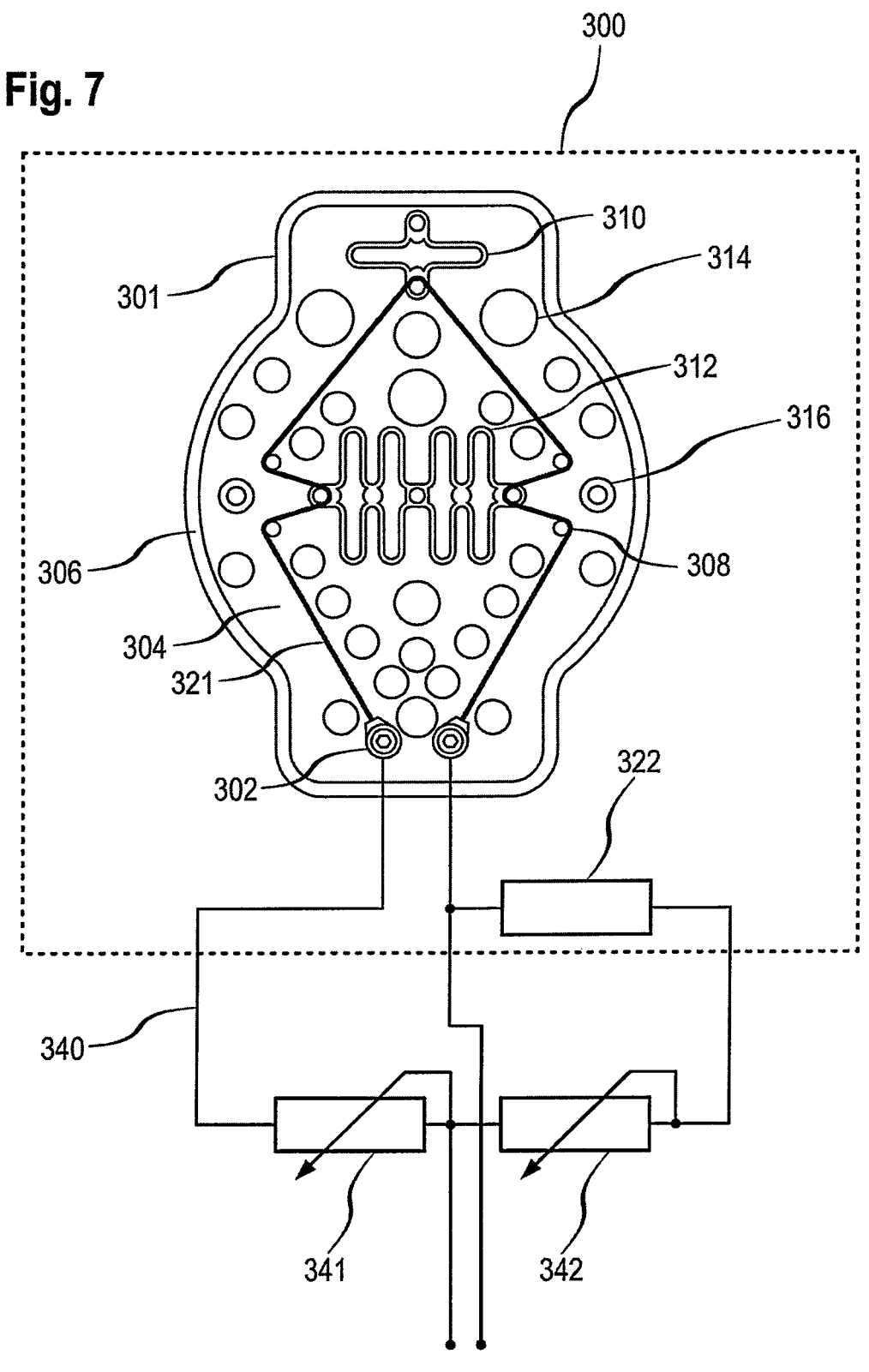

In FIG. 6 and FIG. 7, a measuring bridge 340 according to another embodiment of the present invention is shown. In the measuring bridge 340, one of the voltage dividers is formed by a conductor arrangement 300 according to another embodiment. In the conductor arrangement 300, a first conductor 321, which is formed as a wire and is attached to a support arrangement 301, and a fixed resistor 322 are connected in series. When using this conductor arrangement 300, it is not necessary for the fixed resistor 322 to be brought into contact with the fluid and it is sufficient if only the first conductor 312 is brought into contact with the fluid.

The other of the voltage dividers is formed by two adjustable resistors 341 and 342. The resistors 341 and 342 are resistors whose resistance value can be changed, and they are preferably designed as digital potentiometers. In this embodiment, the evaluation unit 10 is configured to set or change the resistance values of the resistors 341 and 342 such that the measuring bridge 340 is balanced when the AC voltage U0 is initially applied.

Figure 8:
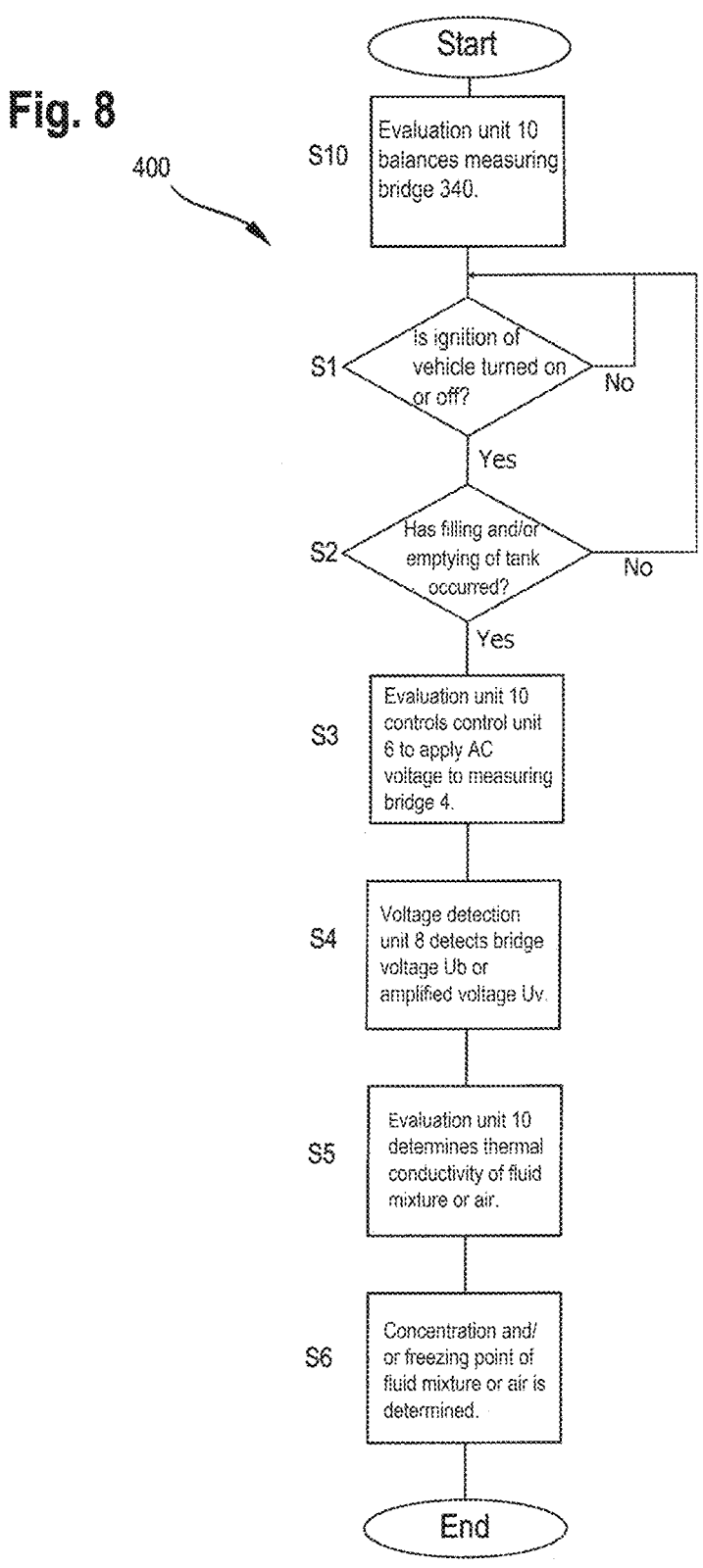
FIG. 8 shows a flowchart of a method for determining a thermal conductivity of a fluid using the fixed resistor.

In this embodiment, the conductor arrangement 300 has only a first conductor 321 that is formed as a wire. The first conductor 321 is connected to leads of the measuring bridge 340 at terminals 302. The terminals 302 in the embodiment shown in FIGS. 8 and FIG. 9 are screw-type terminals, but it is also possible to form the terminals as clamp-type or plug-type terminals. Accordingly, the conductor arrangement can be easily mounted and removed.

In the example shown in FIG. 6 and FIG. 7, the first conductor 321 is laid as a loop and arranged in a plane parallel to a bottom surface 304 of the support arrangement 301. The bottom surface 304 is configured to be flat or planar, for example. A frame 306 is formed around the bottom surface 304, so that the support arrangement 301 is formed as a recessed housing or sleeve in which a small amount of the fluid is present. The first conductor 321 may thus preferably be disposed within the sleeve. By the support arrangement 301 being formed in such a manner, it is achieved that the first conductor 321, which is formed as a wire, is fully surrounded by the fluid over substantially its entire length. Accordingly, detection accuracy is further improved.

The first conductor 321 is passed over one or more deflection points 308 and is biased by means of one or more elastic elements to compensate for a change in length due to heating in the energized state and a change in shape or length of the support arrangement 301 in case of a change in temperature. In the present embodiment, the elastic elements are formed as spring elements 310 and 312. A first spring element 310 biases the first conductor 321 toward an outer side of the loop. A second spring element 312 biases the first conductor 321 toward an inner side of the loop by pulling two opposite portions of the first conductor 321 together by the second spring element 312. In this way, any contact of the first conductor 321 with itself or with other elements of the conductor arrangement 300 is reliably prevented. Consequently, a short circuit of the first conductor 321 can be reliably prevented. In addition, a change in shape or length of the support arrangement due to a change in temperature can be compensated.

Projections 314 or protrusions are again arranged inside and outside the loop of the first conductor 321, which further reliably prevent the first conductor 321 from contacting itself or surrounding elements.

The support arrangement 301 has two hollow cylinders 316 in a central region on the outer sides, into which pins of a lid or cover (not shown) can be inserted or into which screws can be screwed in order to connect the lid to the support arrangement 301. In this regard, the lid rests on the frame 306 of the conductor arrangement 300 and is again formed with slots or holes to allow fluid to enter the interior of the conductor arrangement 300. The lid reduces a risk of mechanical destruction of the support arrangement 301 or the first conductor 321.

The support arrangement 301 is not limited to the first conductor 321, and a second conductor may also be arranged on a similar conductor arrangement. Moreover, the conductor arrangement 300 may also be configured such that both the first conductor and the second conductor are attachable to the conductor arrangement 300. For this purpose, the two conductors can be laid one above the other in two parallel planes, or the second conductor, which has a shorter length than the first conductor, can be formed inside the loop of the first conductor as a loop, too, which may also be pre-stressed by elastic elements.

FIG. 8 shows a flowchart of a method 400 performed when the measuring bridge 340 shown in FIG. 6 and FIG. 7 is used. The method 400 differs from the method 100 shown in FIG. 3 in that a step S10, in which the evaluation unit 10 balances the measuring bridge 340 by adjusting the resistance values of the two resistors 341 and 342, is executed before the step S1.

In this regard, a balancing of the measuring bridge 340 is performed as follows. The evaluation unit 10 is configured to cause at least one of the two transistor booster 10 stages 61, 62 to apply a DC voltage to the measuring bridge 340. In this case, the DC voltage has a value of 200 mV. However, the value of the DC voltage can also be between 100 mV and 500 mV inclusive. The bridge voltage Ub is then detected and the evaluation unit 10 changes the two adjustable resistors 341 and 342. A DC voltage is then again applied to the measuring bridge 340 and the bridge voltage Ub is detected. This process is performed until the bridge voltage Ub detected in response to the applied DC voltage is substantially equal to a voltage of 0 V. Consequently, the measuring bridge 340 can be reliably balanced. This procedure is advantageously and preferably carried out during a first start-up or at a start of a detection of the thermal conductivity in order to initially balance the measuring bridge 340.

Alternatively or additionally, the evaluation unit 10 may be configured to filter out a signal component of the bridge voltage Ub corresponding to the single frequency of the AC voltage U0 applied to the measuring bridge 340. The amplitude of this signal component of the bridge voltage Ub may be used as a measure of the detuning of the measuring bridge 340, and the evaluation unit 10 is configured to change the resistance value of the adjustable resistors 341 and 342 in step S10 such that the signal component of the bridge voltage corresponding to the simple frequency of the applied AC voltage Ub is substantially 0 V. This procedure offers the advantage that any detuning of the measuring bridge 340 can be detected during a measuring operation. Consequently, detuning situations of the measuring bridge 340 that occur, for example, as a result of heating during operation can be detected and the measuring bridge 340 can subsequently be calibrated.

The invention claimed is:

1. A device for determining a leakage of hydrogen from a hydrogen tank, the device configured to be arranged outside a tank space of the hydrogen tank, comprising:

an electrical conductor arrangement which is configured to be brought into contact with a fluid mixture, the conductor arrangement including a voltage divider having first and second elements, the first element being a first conductor which, in a current-carrying state, has a resistance value which is different from that of the second element, the second element being a second conductor, wherein a conductor path corresponding to the first conductor is arranged in a meandering manner between two middle legs of a conductor path corresponding to the second conductor, a measuring bridge comprising two voltage dividers connected in parallel, one of the voltage dividers being formed by the electrical conductor arrangement, a control unit, for applying an AC voltage to the measuring bridge, a voltage detection unit for detecting a bridge voltage, and an evaluation unit configured to:

determine a hydrogen concentration in the fluid mixture based on a thermal conductivity of the fluid mixture, the thermal conductivity being determined by evaluating the bridge voltage using the 3-Omega method, determine the leakage of hydrogen from the hydrogen tank based on the determined hydrogen concentration in the fluid mixture, and output a signal upon determining the leakage.

2. The device according to claim 1, wherein the first conductor and the second conductor have an equal resistance value in a currentless state, and the first conductor reaches a higher temperature than the second conductor in the current-carrying state as the first conductor has a higher resistance value than that of the second conductor in the current-carrying state.

3. The device according to claim 2, wherein the first conductor and the second conductor are arranged in the form of two conductor paths on a circuit board in a meandering manner, and each of the conductor paths includes a plurality of legs and connecting portions between the legs.

4. The device according to claim 1, wherein the second element is a fixed resistor, and the first conductor has, in the current-carrying state, a resistance value which is different from that of the fixed resistor, the other of the voltage dividers of the measuring bridge is formed by two adjustable resistors, and the evaluation unit is configured to adjust the two adjustable resistors before an application of the AC voltage in such a way that the measuring bridge is balanced.

5. A tank arrangement comprising at least one device according to claim 1 and at least one fluid tank which is filled with a fluid, wherein the conductor arrangement of the device is in contact with a gas at least partially surrounding the fluid tank.

6. The tank arrangement according to claim 5, wherein the fluid tank is the hydrogen tank which is filled with hydrogen.

7. The tank arrangement according to claim 5, wherein a plurality of the devices are provided, which are arranged spaced apart from each other outside the tank space of the hydrogen tank.

8. A vehicle comprising a hydrogen propulsion unit and the tank arrangement according to claim 5.

9. A method for determining a leakage of hydrogen from a hydrogen tank by means of the tank arrangement according to claim 5, comprising the following steps:

applying the AC voltage to the measuring bridge, detecting the bridge voltage, determining the hydrogen concentration in the fluid mixture based on the thermal conductivity of the fluid mixture, the thermal conductivity being determined by evaluating the bridge voltage using the 3-Omega method, determining the leakage of hydrogen from the hydrogen tank based on the determined hydrogen concentration in the fluid mixture, and outputting the signal upon determining the leakage.

10. A method for determining a leakage of hydrogen from a hydrogen tank by means of the device according to claim 1, comprising the following steps:

applying the AC voltage to the measuring bridge, detecting the bridge voltage, determining the hydrogen concentration in the fluid mixture based on the thermal conductivity of the fluid mixture, the thermal conductivity being determined by evaluating the bridge voltage using the 3-Omega method, determining the leakage of hydrogen from the hydrogen tank based on the determined hydrogen concentration in the fluid mixture, and outputting the signal upon determining the leakage.

11. The device according to claim 1, wherein a cross-sectional area of the conductor path corresponding to the first conductor is smaller than that of the conductor path corresponding to the second conductor, and the conductor path corresponding to the first conductor is longer than the conductor path corresponding to the second conductor.

* * * * *